United States Patent [19]

Brunell

[11] Patent Number: 5,149,532
[45] Date of Patent: Sep. 22, 1992

[54] METHOD OF VACCINE OR TOXOID PREPARATION AND IMMUNIZATION BY COLONIZATION WITH RECOMBINANT MICROORGANISMS

[75] Inventor: Phillip A. Brunell, Los Angeles, Calif.

[73] Assignee: Cedars Sinai Medical Center, Los Angeles, Calif.

[21] Appl. No.: 430,491

[22] Filed: Nov. 1, 1989

[51] Int. Cl.[5] .................. A61K 39/245; C12N 21/00; C12N 15/38
[52] U.S. Cl. .................................. 424/89; 424/93 A; 435/69.3; 435/172.3; 435/252.3; 435/252.9; 935/12; 935/65; 935/72
[58] Field of Search ................ 435/69.3, 172.3, 252.9, 435/252.3; 424/89, 93; 935/12, 65, 72

[56] References Cited

U.S. PATENT DOCUMENTS 4,888,170 12/1989 Curtiss, III ......................... 424/93

FOREIGN PATENT DOCUMENTS 228726 7/1987 European Pat. Off. ......... 435/252.3

OTHER PUBLICATIONS

Watanabe, Biol. Abstracts vol. 81 (1986) No. 111724.
Amann et al., Gene, 40 (1985) 183-190.

*Primary Examiner*—Jacqueline Stone

[57] ABSTRACT

A method of vaccine or toxoid preparation and immunization against pathogenic disease. An area of the body is colonized with indigenous microorganisms that have been transformed by recombinant DNA technology to express pathogenic antigens. The colonized transformant microorganisms will replicate and elicit an immune response to the pathogenic antigen, thereby protecting the individual from subsequent exposure to the intact pathogen.

3 Claims, No Drawings

METHOD OF VACCINE OR TOXOID PREPARATION AND IMMUNIZATION BY COLONIZATION WITH RECOMBINANT MICROORGANISMS

FIELD OF THE INVENTION

This invention relates to a method of vaccine or toxoid preparation and immunization against pathogenic diseases by colonizing an area of the body with indigenous microorganisms that have been transformed by recombinant DNA technology to express pathogenic antigens. More particularly, this invention relates to a method of vaccine preparation and immunization against Herpes by colonizing the genital tract with lactobacillus that has been transformed by recombinant DNA technology to express the immunologically significant antigens of the Herpes virus.

BACKGROUND OF THE INVENTION

A pathogenic microorganism is any microorganism capable of producing disease, and pathogenicity refers to the ability of the microorganism to gain entrance to a host and produce physiological or anatomical changes. To initiate disease, not only must pathogenic microorganisms enter the body in adequate numbers, but many of them must enter through a certain route called the "portal of entry." This mode of entry differs for each individual microorganism depending on its ability to attack certain cells and tissues. For example, the alimentary tract is the portal of entry for the typhoid and cholera organisms. Tuberculosis, diphtheria, and pneumococcus microorganisms enter through the respiratory tract and may set up infections in the bronchi and lungs. The gonococci, herpes virus, and some other sexually transmitted microorganisms generally enter through the urogenital tract from which they can easily attack the genital organs. Still other organisms enter through abrasions or openings in the skin and set up local infections, or spread through the body in the circulatory system.

Protective immunity is the ability of a host to prevent or overcome invasion by these pathogenic micro-organisms. Immunity may be acquired as a result of the host's recovery from a pathogenic infection, or may be prophylactically induced by administration of a vaccine or toxoid.

Vaccines are suspensions of killed, or living but attenuated microorganisms, or their antigenic portions. Toxoids are detoxified but still antigenically active poisons produced by certain bacteria. Injection of these immunogens (vaccine or toxoid) stimulates an immune response against the specific antigen. Upon subsequent exposure to this same or antigenically related pathogen, the host's immunity assists in defense against the pathogen.

The protection against infection afforded by vaccination operates primarily through the humoral arm of the immune response, with the participation of all major classes of immunoglobulin: IgM, IgA and IgG. Circulating neutralizing IgM, IgA and IgG antibodies interrupt or retard the extracellular dissemination of the pathogen. In addition, the roll of cell-mediated immunity appears to have an effect on the type and intensity of the immune response. Local immunity on the other hand, is restricted to the area of pathogen entry and is mediated by local production and release of IgA antibodies. The secretory IgA antibodies function by neutralizing the pathogen before it makes contact with its target cells, thus preventing implantation and formation of infection. IgG and IgM antibodies also appear in secretions but only in low concentrations.

In developing and administering vaccines or toxoids, the pathogenesis of each particular disease must be considered, since the portal of entry and location of the pathogenic microorganism in the host determine what class of antibody will provide a protective role. In viral respiratory infections, for example, where the focus of the infection is in the ciliated epithelium of the respiratory tract, virus is released mainly on the mucosa surface and does not penetrate into the underlying tissue. As a result, antibodies in the secretions play a major role in the host's defense whereas circulating antibodies participate only insofar as they filter through into the secretions.

A major goal in the prevention of infectious diseases has been the development and use of vaccines or toxoids for immunization. Inactivated and attenuated strains of bacteria and viruses are now widely used for immunization against many diseases including typhoid fever, poliomyelitis, influenza, rabies, measles, and hepatitis type B in humans. (*Manual of Clinical Laboratory Immunology*, 3rd Ed., Rose, Friedman & Fahey, ASM, D.C., 1986). For those bacterial infections where virulence is due in major part to exotoxins such as diphtheria and tetanus, detoxified but antigenically active toxoids can be used to neutralize the toxin. In addition, recent advances in molecular biology and peptide synthesis have allowed production of purified viral proteins or synthetic peptides for use in immunoprophylaxis. (*Fundamental Virology*, Fields & Knipe, Raven Press, NY, 1986).

In most cases, inactivated virus vaccines are prepared from virus that is grown in eggs (influenza type A and B), monkey kidney cell culture (polio virus, types 1, 2 and 3) or human diploid fibroblast cell culture (polio virus, rabies), and then inactivated with formalin. These vaccines offer the advantage of immunization with little or no risk of infection but are considerably less effective than the actual virus infection.

Failure to successfully inactivate vaccine virus has occasionally had serious consequences, as with the formalin-inactivated measles virus vaccine. Initially this vaccine prevented measles, but after several years the vaccinees lost their immunity. When subsequently infected with measles virus, the vaccinees developed an atypical illness with accentuated systemic symptoms and pneumonia. It is believed that the formalin used to inactivate the virus destroyed the antigenicity of the measles F protein, but did not affect the H-protein. The vaccinees developed an unbalanced response that included H-protein immunity but not F-protein immunity. It is also known that inactivated influenza virus vaccine appears to lose its effectiveness after several years, although the basis for this is not known.

Attenuated vaccines contain viable but weakened organisms. They work by producing a mild infection which is usually of little danger to the host. The major advantage of live virus vaccines is their activation of all phases of the immune system; systemic and local, immunoglobulin and cell-mediated. Furthermore, immunity induced by live virus vaccines is generally more durable, more effective and more cross-reactive than that induced by inactivated vaccine. In addition many live virus vaccines are easy to administer and are relatively inexpensive.

The disadvantages of live attenuated virus vaccines include the potential for contamination with live adventitious agents such as other viruses, and the fact that some live virus vaccines, such as the measles virus, rubella virus and yellow fever virus vaccines, retain a low level of residual virulence which may cause mild symptoms of the disease against which the vaccine is directed. More serious problems include those in which rare members of the population are particularly vulnerable to the vaccine strain of the virus, e.g. poliovaccine virus, resulting in paralysis, or where infection by live vaccine virus occurs in immuno deficient individuals. And finally, stability is a serious problem with labile vaccine viruses, and the need for storage and transport of some vaccines at low temperature (measles vaccine) has limited their usefulness in some tropical areas where this maintenance is difficult.

Immunity to infection by pathogenic microorganisms depends on the development of an immune response stimulated by antigens associated with each organism. In some instances, as with viruses, antigens present on the surface of the virus play an important role. In other cases, as with diphtheria or tetanus, immunity is a function of specific antibody to the antigenic toxins produced. Therefore, a successful strategy of immunoprophylaxis against pathogenic diseases requires the generation of an immune response to these "protective antigens", i.e. those antigens that stimulate immunity against the intact pathogenic microorganism.

In recent years, the protective surface antigens important in immunity have been identified for a wide range of viruses (*Fundamental Virology*, Fields & Knipe, Raven Press, N.Y. 1986). With knowledge of the structure or conformation of a particular protective antigen, a synthetic or biosynthetic molecule can be prepared that has the same structure and is capable of provoking antibodies reactive with the intact pathogenic organism.

Two separate approaches have been explored for production of these protective antigens. One involves the production of synthetic peptides which represent immunologically important areas on the surface of the pathogen. The other is recombinant DNA technology which involves splicing a DNA sequence that codes for the pathogenic antigen into a prokaryotic or eukaryotic cell. Subsequently, the cloned pathogen DNA can be expressed in the host cell as pathogen antigen. For example, foot-and-mouth disease virus (FMDV), VP1 capsid protein, hepatitis B virus (HBV) surface antigen, influenza A virus hemagglutinin, rabies virus surface glycoprotein and the gD protein of herpes virus have been expressed in bacteria.

In addition to the potential hazards of vaccines discussed above, there are many other problems associated with current immunization techniques. Some pathogenic microorganisms themselves possess attributes that create uncertainties for developing satisfactory vaccines. For example, many viruses only produce local infections that tend to shield them from the full play of the host's defense system. Also, the inability to grow hepatitis B virus in tissue culture or in animals other than chimpanzees, has prevented the development of a conventional live vaccine. (*Nature*, 302:490–495 (1983)).

The use of protective antigen vaccines is an attractive alternative because it enables circumvention of some of the concerns discussed above that are associated with intact viral immunogens. However, synthesis of relevant protective antigens in bacteria or yeast directed by expression vectors containing cloned DNA copies of the appropriate pathogen genes may not always provide abundant amounts of antigen for use in a vaccine. Many viral antigens (e.g. hepatitis-B virus surface antigen, vesicular stomatitis virus G protein and rabies virus glycoprotein) when expressed in *E. coli*, are either unstable or lethal to the cell. And attempts to directly express the influenza viral surface glycoprotein hemagglutinin (HA) in large quantities using bacterial promoters have failed. (*Proc. Nat. Acad. Sci.,* 78:5376).

SUMMARY OF THE INVENTION

Many indigenous microorganisms abound in and on the human body as well as in animals of other species. Although there is no hard and fast rule which divides these microorganisms into clear-cut categories of harmless, commensal organisms and pathogenic species, microbiologists have attempted to list and categorize them accordingly. Microorganisms that exist in conjunction with the host, resist the host's defense mechanisms but at the same time are unable to invade body tissues. These microorganisms are capable of colonizing various areas of the host and are generally regarded as normal inhabitants.

Among those microorganisms indigenous to the mouths of healthy individuals are the staphylococci, micrococci, viridans streptococci, enterococci and lactobacilli. These organisms exist in the mouth in the interstices between the teeth, and in and under tooth plaques. The bacteria commonly present in the nose and throat consist of still different forms such as pneumococci and streptococci, and the bacterial types present in the intestine are determined to a considerable extent by the type of food material present which varies with diet and pH. Although many organisms can be cultured from the normal female genital tract, the usual aerobic microflora is dominated by the lactobacilli. (*Manual of Clinical Microbiolgy,* 2nd Ed., Lennette, Spaulding and Truant, eds., American Society for Microbiology, Washington, D.C. 1974).

We propose a method of immunization against pathogenic disease by colonizing an area of the body with these indigenous microorganisms that have been transformed by recombinant DNA technology to express protective antigens. The colonized transformant microorganisms will replicate at the mucosal surface thereby eliciting an immune response to the protective antigen and protecting the individual from subsequent exposure to the intact pathogen.

DETAILED DESCRIPTION

Although the method described in my invention may be used to immunize an individual against any known pathogen, a preferred embodiment is for immunization against the herpes simplex virus (HSV). The following description therefore, is mainly directed to immunization against HSV, but the invention is not intended to be restricted to this use.

Herpes simplex viruses are among the most common infectious agents of man. The number of new cases of herpes infections per year is not known precisely, but minimally it is estimated to be several hundred thousand (JAMA 253:1601 (1985)). There are at least two distinct serotypes of the virus, HSV-1 and HSV-2. Both serotypes cause persistent and latent infections, including recurrent cutaneous disease and viral encephalitis.

There have been numerous attempts to develop vaccines against HSV-2. Concern about producing latent infections with attenuated live vaccines has shifted attention toward killed and more specifically subunit vaccines. The principle candidate for these subunit vaccines is HSV glycoprotein D (HSV gD), the major structural antigen of the virus responsible for the induction of humoral and cellular immunity (*J. Virol.* 41:478 (1982)). However, recent controlled trials of a parenterally administered HSV gD vaccine has produced somewhat disappointing results (Abstracts, ICAAC, 1987).

Although most effort has focused on development of the antigenic components of a vaccine, there has also been some interest in the route of vaccine administration, and whether immunization at the site of infection might have an advantage over parenteral administration. In general, antigens given parenterally are believed less able to stimulate immunity at the mucosal surfaces (*J. Clin. Immuno* 7:265 (1987)). Clinical data moreover, suggest that parenteral immunization against *V.cholera* may suppress the mucosal response to locally applied antigens (*J. Immuno* 124:307 (1980)). However, mice immunized intravaginally with thymidine kinase negative strain of HSV-2 were found to be protected against an intravaginal challenge that was lethal to unimmunized control mice. (*J. Virol.* 51:747 (1984)).

The lactobacilli are the most common aerobic organisms found in the vagina of the human. Metchnikoff proposed that the lactobacillus is essential for well being (ASM News 54:12 (1988)), and Reid et al. found that the organisms may even protect against urinary tract infection. (*Infec. Immun.* 49:230 (1985)). Additionally, lactobacilli are found normally in the male urethra (*J. Clin. Microbiol.* 6:482 (1977)).

I propose a vaccine for immunizing an individual against HSV by colonizing the female genital tract with an indigenous strain of lactobacillus that has been transformed by recombinant DNA technology to express HSV glycoproteins. This technique may also be applicable to the male by colonizing the urethra.

Recent developments of a host vector system for lactobacilli make it possible to introduce genes into these bacteria (*FEMS Micro Rev.* 46:297-312 (1987)). The recombinant lactobacillus of my invention contains a promoter, an alpha-amylase gene, a structural gene coding for the protective antigen, and a marker to establish whether the insertion of the gene has been successful and is in the correct reading frame. The amylase portion results in the secretion of the attached HSV gD, by the lactobacillus. A beta galactosidase marker is used rather than an antibiotic resistant marker to avoid colonization and potential spread of an antibiotic resistant strain of lactobacillus. Alternatively an antibiotic resistant gene can be used and the antibiotic to which the organism is resistant used to eliminate existing flora to favor the survival of the colonizing resistant strain.

The vectors useful for strain construction in lactobacilli have been previously described as efficient vehicles for cloning in many lactobacillus strains. (*FEMS Microbiol. Revs.* 46:297-312 (1987); *J. Clin. Microbiol.* 6:482 (1977); *Infec. Dis. Clin. of N. Amer.* 2(1):1 (1988); *Trends. Biotechnol.* 3:273-275 (1985); *Biochimie* 70:503-517 (1988)). The method of the invention involves inserting genes for the glycoproteins of herpes simplex viruses via a vector into strains of lactobacilli that have been shown to normally be the predominant species in the vagina (or urethra in the male). The recombinant lactobacilli are screened in solid media for the HSV gD insert by the production of beta galactosidase and then by hybridization of the nitrocellulose paper lifts with the HSV gD fragment. Positive colonies are picked, cultured, and tested for expression of HSV gD by fixing cells and incubating them with an anti-HSV gD antibody and then staining them with fluorescein conjugated immunoglobulin. They are then mounted on slides and examined by fluorescence microscopy. In addition, the bacteria or bacterial broth can be tested for HSV gD in an ELISA system or a polyacrylamide gel and Western blot. In either case, an antibody against HSV gD may be used in the detection system.

The recombinant lactobacilli are inoculated into the vagina. Presence of infection in the colonized animal model is determined by flushing the vagina at daily intervals with lactobacillus carrying medium (LCM), an aliquot of which is plated immediately onto an agar plate using an LCM base (*J. Microbiol.* 48:994 (1984)). After incubation overnight at 37° C., lifts are made with nitrocellulose paper hybridized to a nick-labeled HSV gD probe. The proportion of colonies containing the insert and their rate of disappearance are then calculated.

The production of an immune response to the herpes simplex virus is established by testing vaginal secretions and serum for the presence of antibody against herpes. This is done by modifying the anti-HSV ELISA which we described previously. (*J. Clin. Microbiol.* 26:781 (1988)). Testing for IgA is done using an anti-alpha conjugate and anti-mouse rather than anti-human reagents. The seronegative range is established by testing vaginal secretions and sera of mice prior to inoculation. Testing is performed starting at one week following colonization and repeated weakly.

When there is evidence of an immune response to HSV gD, the animals are then challenged intravaginally with a dose of herpes virus which has been shown to produce death, latent infection, or other clinical signs of herpes vaginitis in unprotected mice. The effectiveness is studied by comparing mortality, latent virus infection of spinal ganglia, and virus shedding in unprotected mice and in mice inoculated with lactobacilli containing the gene for herpes virus glycoproteins.

EXAMPLE 1

Preparing the Constructs

The structural gene for HSV gD is cloned in a vector suitable for transformation of Lactobacilli. It is preferable to start with a vector with a multi-cloning region. To this is added the promoter and secretion leader sequence of the alpha-amylase gene of *Bacillus amyloliquifaciens* in order to direct secretion of HSV gD. One skilled in the art will know that other promoter sequences that function in Lactobacilli can be substituted for the alpha-amylase promoter sequence. The HSV gD structural gene is then inserted in the correct reading frame with the promoter and secretion leader sequence.

The HSV gD gene is mutagenized and truncated using synthetic oligonucleotides, and the new sequence is verified by DNA sequencing. The truncated form is relegated into a vector with the appropriate promoter and secretion leader sequences.

One skilled in the art will recognize that this forced cloning is designed to be orientation specific and produce in-frame translational fusions of the alpha-amylase secretion leader to the HSV gD gene product, so that any other available technique may be used. The ligation mixtures are transformed into *L. casei* by electroporation as described by Chassy (*Trends Biotechnol.* 3:273-275 (1985)).

The transformed mixtures are inoculated into Lactobacillus carrying medium (LCM) and allowed to develop for two hours at 37° C. Portions are spread on LCM plates containing 10 μg/ml chloramphenicol (cm), and the plates incubated for two days at 37° C. in a Gas-Pack (BBL). Colonies (transformants) are streaked onto LCM-Cm plates for purification. One skilled in the art will recognize that alternatively, the colonies can be "lifted" onto nitro-cellulose and probed by DNA-DNA hybridization for the presence of HSV gD coding sequences. The HSV gD-containing restriction fragment described above (i.e. EcoRI to Hind III) is radiolabeled by the random priming technique and used as a probe for colonies containing the HSV gD gene.

Cultures of random transformant colonies, or those hybridizing to the HSV gD gene probe, are analyzed for plasmid content by the standard procedure for Lactobacilli known in the art. Using agarose gel analysis of restriction enzyme digests of plasmids isolated from transformants, the screening will ascertain if the HSV gD gene has been inserted in the correct orientation and verify that the entire coding sequence was inserted. One skilled in the art will know the unique restriction sites available to analyze a correct cloning sequence that carries the alpha-amylase gene fused to the intact HSV gD polypeptide coding sequences.

One skilled in the art will recognize that the constructs described above can be made in *E. coli* using pNZ12 and its derivatives as a shuttle vector, and then subsequently transferred to *L. casei* or other predominant strain of lactobacillus in the vaginal flora. Alternatively, pIL253 can be employed for direct cloning in Lactobacilli.

EXAMPLE 2

Testing the Constructs for HSV gD Synthesis

Selected clones carrying the desired recombinant construction described in Example 1 above, are cultivated in 1 liter LCM-10 μg/ml chloramphenicol cultures at 37° C. for 18 hours. Control cultures contain only the vector. The bacteria are collected by centrifugation and separated from the growth medium. The growth medium is concentrated to 10 ml and dialyzed against phosphate buffered saline (PBS).

To determine cell-associated HSV gD, a sample of the bacteria is assayed directly by UV-microscopy and by analysis of the disrupted cell contents. The HSV gD present in the growth medium is also analyzed. These procedures follow:

(1) The bacteria are resuspended in PBS, centrifuged and washed in PBS three times. A small sample of bacteria in the final pellet is placed on a microscope slide and air dried at room temperature. The bacteria are then fixed, incubated with rabbit anti-HSV gD antibody, rinsed with PBS, incubated with fluoscein-conjugated anti-rabbit globulin, rinsed, mounted in alkaline glycerol buffer and examined for fluorescence by fluorescence microscopy.

(2) An aliquot of the washed pellet bacteria above is disrupted in a glass bead mill (Biospec, Barthesville, Okla.) The cell debris and insoluble material are sedimented by centrifugation. The bacterial supernatant will be analyzed as in (3) below.

(3) The bacterial supernatant from (2) and the dialyzed concentrated growth medium are diluted 1:1 with electrophoresis sample buffer. The HSV gD protein is separated on 11% SDS polyacrylamide gels and transferred to nitrocellulose membrane by electroblotting at 100 V for 2.5 hours. The membrane is washed in PBS containing 0.3% Tween-20 (PTB), reacted overnight with a solution of PTB containing 4% normal goat serum and rabbit anti-gD, washed with PTB, incubated with biotinylated goat anti-rabbit IgG, washed with PTB, and reacted with streptavidin-horseradish peroxidase, or streptavidin-alkaline phosphatase. Color is developed with 4-chloro-1-naphol (for horseradish peroxidase) or 5-bromo-4-chloro-3-indolyl phosphate p-toluidine salt/nitroblue tetrazolium chloride (for alkaline phosphatase).

The gel lanes are as follows: (1) the concentrated growth medium supernatant from the transformed lactobacilli, (2) the bacterial supernatant from lysed transformed lactobacilli, (3) HSV gD control, (4) the broth from non-transformed cultures of lactobacillus, (5) bacterial supernatants from lysed nontransformed cultures of lactobacillus and (6) molecular weight markers. Presence of the amylase - HSV gD fusion protein in the supernatant from lysed transformed lactobacilli confirms that the organisms are producing HSV gD. Presence of the amylase - HSV gD fusion protein in the growth medium supernatant confirms that the organisms are producing and secreting HSV gD.

EXAMPLE 3

Method of Colonization

Six-week old female BALB/CJ mice are used since one skilled in the art would appreciate that susceptibility of younger mice to intravaginal challenge with HSV-2 appears to vary directly with age. (*Arch Virol.* 93:51 (1987)).

A log-phase broth of transformed lactobacilli is centrifuged at 800 xg. A volume of the pellet is serially diluted and the number of organisms estimated by an opacity standard. Since one skilled in the art would appreciate that the estimated human vagina contains approximately $10^7$ organisms/ml (*Rev. Inf. Dis.* 134:486-489 (1976)), at least this number of organisms is placed in the mouse vagina in a volume of 0.010 ml.

EXAMPLE 4

Determining Whether Colonization Has Been Accomplished

Colonization of the mice with the transformed lactobacilli is determined by scraping the wall of the vagina with a calibrated loop, and immediately streaking for colony count on agar plates with a base of LCM. Samples are obtained every third day following colonization for 2 weeks.

The agar plates are incubated overnight at 37° C. and the total number of colonies counted. Lifts are made with nitro cellulose paper which is hybridized to a nick-labelled HSV gD probe. The proportion of colonies containing the HSV gD insert is calculated by the number of radiolabeled colonies per total number of colonies. The rate of persistence is computed by determining this ratio at increasing intervals following colonization of the animals.

EXAMPLE 5

Determining An Immune Response To HSV gD

The immune response to HSV gD produced by the transformed colonizing bacteria is measured by testing both blood and vaginal secretions for anti-HSV gD antibody. Secretions are collected by flushing the vagina with 0.015 ml aliquots of TRIS buffered saline (pH 7.4) and aspirating. Blood specimens are collected and serum separated by standard techniques.

The anti-HSV gD antibody is detected by modification of an ELISA system previously described. (*J. Clin. Micro.* 26:781 (1988)). Plates are coated with HSV gD or control, and rinsed. Diluted specimens (blood or vaginal secretions) are added, incubated and rinsed. Anti-mouse IgA conjugated to alkaline phosphatase is added, incubated, and rinsed. Substrate is added and incubated, followed by sodium hydroxide to stop the reaction. The color developed is read at 405 nm.

Testing of the mice for anti-HSV gD antibody is started at one week following colonization and repeated weekly. When animals become seropositive, they are tested until two successive samplings show no increase in antibody. Then, the animals are challenged with HSV-II. (See Example 6).

EXAMPLE 6

Virus Challenge

When there is evidence of an immune response to HSV gD (see Example 5), mice are challenged with HSV-2 strain 333, a human isolate adapted for use in mice.

A titration in unprotected mice is performed using a vaginal inoculum of 0.01 ml containing $10^2$ to $10^6$ pfu of HSV-2. Plaque titrations are done in vero cells using an assay previously described. (*J. Clin. Micro.* 14:376-379 (1984)). A dose of HSV-2 sufficient to produce death in 50% of the unprotected animals challenged intravaginally (i.e. one $LD_{50}$) is used in the challenge experiments.

The effect of the vaccine is judged by three criteria: (1) mortality, (2) latent infection of spinal ganglia, and (3) vaginal infection with HSV-2.

To test for spinal ganglia infection, bilateral spinal ganglia are removed from the mice at three weeks after infection. The ganglia are minced and placed directly on a cell monolayer which is observed for c.p.e. (*Infec. and Immunity*, 16:69-74 (1977)).

To detect vaginal infection, titers of HSV-2 in vaginal specimens of mice colonized with the transformed lactobacillus are compared to the control mice. Vaginal swabs are obtained at 2 day intervals for 8 days following inoculation with HSV. The swabs are placed in 1 ml of tissue culture fluid, separated into aliquots and frozen at $-70°$ C. Virus is then tittered by the plaque assay described above, and the quantity of virus in the colonized and uncolonized control animals compared. Failure to detect HSV-2 in the colonized mice indicates that infection has been prevented.

Other and further embodiments of the invention are readily apparent from the above description of the invention, and these embodiments are believed to be within the scope of the invention.

I claim:

1. A method of preparing a vaccine against herpes simplex virus comprising:
   a) transforming lactobacillus by recombinant DNA technology to express herpes simplex virus glycoprotein D;
   b) growing said lactobacillus in a suitable culture medium; and
   c) harvesting said lactobacillus by separating it from said culture medium.

2. A vaccine against herpes simplex virus which comprises lactobacilli that have been transformed by recombinant DNA technology to express herpes simplex virus glycoprotein D.

3. A method of immunizing a host against herpes simplex virus comprising:
   a) transforming lactobacillus by recombinant DNA technology to express herpes simplex virus glycoprotein D (HSV gD);
   b) culturing and harvesting said lactobacillus; and
   c) colonizing the genital tract with said lactobacillus such that the expressed HSV gD will elicit an immune response to the herpes simplex virus.

* * * * *